United States Patent [19]

Khodzhakhanov et al.

[11] 4,138,425

[45] Feb. 6, 1979

[54] METHODS OF PREPARING ANION SURFACE-ACTIVE SUBSTANCES

[76] Inventors: Nabi A. Khodzhakhanov, ulitsa Samrkand-Darbaza, proezd Termez, 8/62a; Takhir M. Makhmudov, ulitsa Ivleva, 26; Karim S. Akhmedov, proezd Morozova, 1/8, kv. 17, all of Tashkent, U.S.S.R.

[21] Appl. No.: 849,982

[22] Filed: Nov. 9, 1977

Related U.S. Application Data

[63] Continuation of Ser. No. 226,307, Feb. 14, 1972, abandoned.

[51] Int. Cl.$^2$ ............... C07C 141/16; C07C 141/18; C11D 1/22
[52] U.S. Cl. ............................ 260/458 C; 252/545
[58] Field of Search ................................. 260/458 C

[56] References Cited

U.S. PATENT DOCUMENTS

| 2,758,977 | 8/1956 | Knowles et al. | 260/458 |
| 3,265,722 | 8/1966 | Dudley | 260/458 |
| 3,332,979 | 7/1967 | Redemann | 260/458 |
| 3,376,333 | 4/1968 | Ernst et al. | 260/458 |
| 3,393,219 | 7/1968 | Myerly et al. | 260/458 |

FOREIGN PATENT DOCUMENTS

| 982600 | 1/1967 | Canada | 260/458 |
| 1142602 | 1/1963 | Fed. Rep. of Germany | 260/458 |

OTHER PUBLICATIONS

Kirk–Othmer, Encyclopedia of Chemical Technology, vol. 15, pp. 8 and 9, and vol. 14, pp. 850 and 851, (1968).
Suga et al., J. Chem. Soc. Japan, Ind. Chem. Sect., vol. 70, pp. 487 to 491, (1967).

*Primary Examiner*—Joseph E. Evans
*Attorney, Agent, or Firm*—Haseltine, Lake & Waters

[57] ABSTRACT

A method for preparing anion surface-active substances consists in that phenol extract, obtained in petroleum distillation at temperatures within the range from 360 to 500° C, is alkylated with propylene oxide in the presence of a metal halide.

Thus obtained alkyl aromatic alcohols, having the number of carbon atoms from 22 to 32, are sulphoesterified with sulphamic acid in the presence of urea in a medium of organic solvents. The anion surface-active substances are finally recovered from the esterificate by extraction with lower aliphatic alcohols. The anion surface-active substances have the following general formula: R—Ar—(CH$_2$)$_3$—O—SO$_3$NH$_4$, where R is an aliphatic radical having the number of carbon atoms from 9 to 15 and Ar is a mixture of benzene, naphthalene, and anthracene.

One per cent aqueous solutions of the proposed anion surface-active substance reduce the surface tension of water to 27 – 28 erg/sq.cm.

7 Claims, No Drawings

METHODS OF PREPARING ANION SURFACE-ACTIVE SUBSTANCES

This is a continuation of application Ser. No. 226,307 filed Feb. 14, 1972 and now abandoned.

This invention relates to methods for preparing anion surface-active substances used as detergent in domestic chemistry, as a floating agent in metallurgy, as stabilizers of mud fluids and antifoam agents.

Anion surface-active substances, like alkyl aryl sulphonates and alkyl aryl sulphanoles are widely known in the prior art. Alkyl aryl sulphonates are produced on the basis of paraffin hydrocarbons or alkyl aromatic hydrocarbons. Paraffin hydrocarbons are treated with sulphuric acid or sulphur dioxide to obtain sulpho acids, which are then processed with alkalies into anion surface-active substances.

Another method for preparing anion surfactants consists in alkylation of benzene with a mixture of olephins in the presence of aluminium chloride as catalyst. Thus prepared alkyl benzenes are sulphonated with oleum at a temperature from 5 to 10° C., and the resulting alkyl aryl aromatic acids are processed with alkalies into anion surface-active substances.

The alkyl aryl sulphanoles are prepared as follows.

Paraffin hydrocarbons are oxidized with atmospheric oxygen, in the presence of boric acid or its esters as catalysts, at a temperature from 105 to 110° C. Thus obtained esters are decomposed into a mixture of aliphatic alcohols which are then treated with sulphuric acid, and alkalies to prepare alkyl aryl sulphanoles.

Benzene and its homologues are alkylated with a mixture of olefins in the presence of aluminium chloride as a catalyst. The obtained alkyl benzene is alkylated with ethylene oxide to prepare alkyl aromatic alcohols which are treated with sulphuric acid and then with alkali to prepare alkyl aryl sulphanoles.

Anion surface-active substances-ammonium alkyl sulphates are also known. They are prepared by treating alcohol fractions $C_{10}$–$C_{18}$ with sulphamic acid in the presence of urea as catalyst and dimethyl formamide as solvent.

The analysis of the mentioned methods shows that the prior-art process for preparing anion surface-active substances comprises many steps and requires expensive starting materials, like alcohol, benzene and olefins.

The object of this invention is to work out a method for preparing anion surface-active substances from easily available and cheap materials, and also to widen the list of the existing surfactants.

The anion surface-active substances according to the invention are entirely new organic compounds which have not so far been described in the literature.

The proposed anion surface-active substances have the general formula R — Ar — $(CH_2)_3$ — O — $SO_3NH_4$, where R is an aliphatic radical having the number of carbon atoms from 9 to 15 and Ar is a mixture of benzene, naphthalene and anthracene.

The anion surface-active substances according to the invention are white crystalline products having the melting point of 355–358° C., the molecular weight of 474–475, readily soluble in water and lower aliphatic alcohols, in ethyl alcohol in particular. At 20° C. one percent aqueous solutions reduce the surface tension of water to 27–28 erg/sq.cm.

Phenol extracts, which are the bottoms of the petroleum distillation process, are used as the starting materials in the manufacture of the proposed surfactants.

The essence of the method according to the invention consists in the following.

The phenol extract obtained in the petroleum processing at temperatures from 360 to 500° C. is alkylated with propylene oxide according to the Friedel Crafts reaction in the presence of aluminium chloride, or zinc chloride, cupric chloride or ferric chloride as catalysts.

The reaction of alkylation is carried out at atmospheric pressure (760 mm Hg) and ordinary temperature, but it is desirable that the reaction mixture should be somewhat heated, for example to 40° C., in order to accelerate the process. Thus prepared alkyl aromatic alcohols, having the number of carbon atoms from 22 to 32, are then reacted with sulphamic acid in a medium of organic solvents, e.g. petroleum ether, aviation petrol, benzene and its homologues. The final product is recovered from the reaction mixture by extraction with lower aliphatic alcohols.

Use can be made of other similar solvents, viz. solvents in which the said alkyl aromatic alcohols are soluble and the reaction between the components is more effective. The sulphoesterification reaction should be carried out in the presence of urea which is a catalyst in this process. The preferable temperature of the sulphoesterification is 110–115° C. This intensifies the process, which lasts for 1.5-2 hours, and increases the yield of the product to 85%. Unless heated, the components react at a slower rate and the yield is lower too. The alkyl aromatic alcohols and sulphamic acid are taken for the sulphoesterification process in a molar ratio of 1:1.

The "phenol extract", used as the basic starting material, is a product obtained in the process of petroleum distillation. The extract is a dark brown thick mass having the following specifications: $d_4^{20} = 0.9766$, $n_D^{20} = 1.5230$, mean molecular weight 352, the melting point 360–500° C. The extract is actually the still residue, or bottoms, that remain in distillation of various petroleums.

The advantages of the proposed method for preparing anion surface-active substances are as follows.

1. The proposed surfactants have better physicochemical and surface-active properties. They are readily soluble in water and alcohol (without reside), which improves their washing properties. One percent aqueous solutions of the product reduce the surface-tension of water to 27–29 erg/sq.cm.

The known similar surface-active substances produce emulsions with water and leave stains in textile fabrics that are washed in the presence of such emulsions. One percent aqueous solutions of the prior art surfactants reduce the surface tension of water only to 30–32 erg/sq.cm.

The process according to the invention reduces the cost of production compared with the prior art methods.

2. The proposed method for preparing anion surface-active substances provides the conditions for carrying out the alkylation and sulphoesterification reactions at moderate temperature and in short lapses of time (1.5-2 hours), which is also a favourable condition for automation of the process.

3. The starting material for the preparation of anion surface-active substance is the phenol extract, which is a cheap material available at oil refineries in ample quantities.

For a better understanding of the invention, the following examples of practical embodiment of the proposed process for preparing anion surface-active substances are given by way of illustration.

EXAMPLE 1

A mixture of 300 g of phenol extract obtained in petroleum distillation at temperature from 360 to 500° C., 20 g of ammonium chloride and 60 ml of propylene oxide (which are added gradually to the mixture at a temperature of 30° C.) is loaded into a reaction kettle equipped with a reflux condenser and a stirrer, and kept there for two hours. On the termination of the alkylation reaction, the mixture is cooled and washed with water three times to remove the catalyst.

Then, 5.4 g of urea, 86 g of sulphamic acid and 300 ml of petroleum ether are added, the mixture is heated to a temperature of 115° C. and kept for two hours. On the termination of the sulphoesterification process, the reaction mixture is cooled and dissolved in a 25 percent aqueous solution of isopropyl alcohol. As a result, the mixture is separated into two layers, the lower one containing an aqueous-alcoholic solution of the anion surface-active substances, which are then recovered by vacuum distillation of the solvent and water. The yield of the product is 85 percent of theory.

The elementary analysis of the obtained anion surface-active substances having the empirical formula $C_{27}H_{41}NO_4S$ is as follows:

Found, in percent: C 67.92; H 8.41; C 12.83; S 6.10; N 2.41. Calculated, in percent: C 68.21; H 8.63; O 13.57; S 6.62; N 2.97.

EXAMPLE 2.

The process for preparing anion surface-active substances is carried out as described in Example 1, except that zinc chloride is used as the catalyst. The yield of the anion surface-active substances is 83 percent of theory.

EXAMPLE 3.

The process for preparing anion surface-active substances is carried out as described in Example 1, except that ferric chloride is used as the catalyst. The yield of the anion surface-active substances is 82.5 percent of theory.

EXAMPLE 4.

The process for preparing anion surface-active substances is carried out as described in Example 1, except that a 25 percent of aqueous solution of ethyl alcohol is used to extract the product. The yield of the anion surface-active substances is 85 percent of theory.

EXAMPLE 5.

The process for preparing anion surface-active substances is carried out as described in Example 1, except that a 20 percent aqueous solution of nonyl alcohol is used to extract the product. The yield of the product is 85 percent of theory.

EXAMPLE 6.

The process for preparing anion surface-active substances is carried out as described in Example 1, except that the reaction of sulphoesterification is carried out with aviation petrol. The yield of the anion surface-active substances is 85 percent of theory.

EXAMPLE 7.

The process for preparing anion surface-active substances is carried out as described in Example 1, except that the reaction of sulphoesterification is effected in a medium of toluene. The yield of the anion surface-active substances is 85 percent of theory.

We claim:

1. Anion surface-active substances having the general formula $R — Ar — (CH_2)_3 — O — SO_3NH_4$, wherein R—Ar is a radical resulting from phenol extracts obtained from the bottoms of petroleum distillation where R is an aliphatic radical having the number of carbon atoms from 9 to 15 and Ar is a mixture of benzene, naphthalene and anthracene radicals.

2. A method for preparing anion surface-active substances having the formula $R—Ar—(CH_2)_3—O—SO_3NH_4$, wherein R—Ar is a radical resulting from phenol extracts obtained from the bottoms of petroleum distillation at temperatures of from 360 to 500° C. wherein R is an aliphatic radical of from 9 to 15 carbon atoms and Ar is a mixture of phenylene, naphthalene and anthracene radicals; comprising the steps of alkylating said phenol extract, with propylene oxide in the presence of a Friedel Crafts reaction metal halide catalyst, reacting the thus-obtained alkyl aromatic alcohol product, having from 22 to 32 carbon atoms, with sulphamic acid in the presence of a urea catalyst in a medium of organic solvents, and recovering the final product from the reaction mixture by extraction with lower aliphatic alcohols.

3. A method according to claim 2, wherein the phenol extract is alkylated in the presence of aluminium chloride as catalyst.

4. A method according to claim 2, wherein the alkyl aromatic alcohol product and the sulphamic acid are reacted in a molar ratio of 1:1 at a temperature from 110 to 115° C.

5. A method according to claim 2, wherein the solvent medium is selected from the group consisting of dimethyl formamide, petroleum ether, benzine, benzene and its homologues.

6. A method according to claim 2, wherein the final product is extracted from the reaction mixture with an alcohol, selected from the group consisting of methyl, ethyl, propyl, isopropyl, butyl and isobutyl alcohols.

7. A method for preparing anion surface-active substances having the formula $R—Ar—(CH_2)_3—O—SO_3NH_4$, wherein R—Ar— is a radical resulting from phenol extracts obtained from the bottoms of petroleum distillation at temperatures of from 360 to 500° C. wherein R is an aliphatic radical having from 9 to 15 carbon atoms and Ar is a mixture of phenylene, naphthalene and anthracene radicals; comprising the steps of alkylating said phenol extract with propylene oxide in the presence of a Friedel Crafts reaction metal halide catalyst, reacting the thus-obtained alkyl aromatic alcohol product having from 22 to 32 carbon atoms with sulphamic acid in the presence of a urea catalyst.

* * * * *